(12) United States Patent
Marcolongo et al.

(10) Patent No.: US 8,110,212 B2
(45) Date of Patent: Feb. 7, 2012

(54) BIOACTIVE THERMOGELLING POLYMER SYSTEMS AND METHODS OF THEIR USE

(75) Inventors: Michele Staud Marcolongo, Aston, PA (US); Anthony M. Lowman, Wallingford, PA (US); Emily Y. Ho, Morristown, NJ (US)

(73) Assignee: Drexel University, Philadelphia, PA (US)

( * ) Notice: Subject to any disclaimer, the term of this patent is extended or adjusted under 35 U.S.C. 154(b) by 833 days.

(21) Appl. No.: 11/910,494

(22) PCT Filed: Apr. 7, 2006

(86) PCT No.: PCT/US2006/012830
§ 371 (c)(1),
(2), (4) Date: Jun. 19, 2008

(87) PCT Pub. No.: WO2006/110448
PCT Pub. Date: Oct. 19, 2006

(65) Prior Publication Data
US 2009/0269384 A1    Oct. 29, 2009

Related U.S. Application Data

(60) Provisional application No. 60/668,993, filed on Apr. 7, 2005.

(51) Int. Cl.
*A61K 9/10* (2006.01)
*A61K 47/32* (2006.01)
(52) U.S. Cl. ............... 424/423; 523/116; 514/772.4
(58) Field of Classification Search ............... 424/423; 523/116; 514/772.4
See application file for complete search history.

(56) References Cited

U.S. PATENT DOCUMENTS
2004/0220296 A1    11/2004    Lowman et al.

FOREIGN PATENT DOCUMENTS
WO    WO 98/43615    * 10/1998
WO    WO 98/43615 A1    10/1998

OTHER PUBLICATIONS

Kamitakahara et al., Biomaterials 22 (2001) 3191-3196.*
Fribourg, D., et al., "Incidence of subsequent vertebral fracture after kyphoplasty," The Spine Journal, 2003. 3(95S).
Hillmeier, J., et al., "Kyphoplasty with a new biological calcium phosphate cement," The Spine Journal, 2003, 3, (117S).
Kokubo, T., H.-M. Kim, and M. Kawashita, "Novel bioactive materials with different mechanical properties," Biomaterials, 2003. 24(13): p. 2161-2175.
Rea, S.M., et al. "Proliferation and differentiation of osteoblast-like cells on apatite-wollastonite/polyethylene composites," Biomaterials, 2004. 25(18): p. 4503-4512.
Juhasz, J.A., et al. "Mechanical properties of glass-ceramic A-W-polyethylene composites: effect of filler content and particle size," Biomaterials, 2004. 25(6): p. 949-955.
Kamitakahara, M., et al. "Effect of polyacrylic acid on the apatite formation of a bioactive ceramic in a simulated body fluid: fundamental examination of the possibility of obtaining bioactive glass-ionomer cements for orthopaedic use," Biomaterials, 2001. 22(23): p. 3191-3196.
Ren, L., et al., "Sol-gel preparation and in vitro deposition of apatite on porous gelatin-siloxane hybrids," Journal of Non-Crystalline Solids, 2001. 285(1-3): p. 116-122.
Kokubo, T., "Apatite Formation on Surfaces of Ceramics, Metals and Polymers in Body Environment," Acta Materialia, 1998. 46(7): p. 2519-2527.
Ohya, S., S. Kidoaki, and T. Matsuda, Biomaterials, "Poly(N-isopropylacrylamide) (PNIPAM)-grafted gelatin hydrogel surfaces: interrelationship between microscopic structure and mechanical property of surface regions and cell adhesiveness," 2005. 26(16): p. 3105-3111.
Katz, J., Composite Materials Models for Cortical Bone, in Mechanical Properties of Bone, S. Cowin, Editor. 1981, Ed. A.S.M.E.: NY. p. 171-184.
Combes, C. and C. Rey, Biomaterials, "Adsorption of proteins and calcium phosphate materials bioactivity," 2002. 23(13): p. 2817-2823.
El-Ghannam, A., "Advances bioceramic composite for bone tissue engineering: Design principles and structure-bioactivity relationship," Journal of Biomedical Materials Research, 2004. 169A(3): p. 490-501.
Hench, L.L., Bioceramics. Journal of the American Ceramic Society, 1998. 81: p. 1705-28.
Yao, J., et al., The effect of bioactive glass content on synthesis and bioactivity of composite poly (lactic-co-glycolic acid)/bioactive glass substrate for tissue engineering. Biomaterials, 2005. 26(14): p. 1935-1943.
Marcolongo, M., et al., Bioactive glass fiber/polymeric composites bond to bone tissue. Journal of Biomedical Materials Research, 1998(39): p. 161-170.

* cited by examiner

*Primary Examiner* — Robert D. Harlan
(74) *Attorney, Agent, or Firm* — Woodcock Washburn, LLP

(57) ABSTRACT

Hydrogels comprising poly(N-alkylacrylamide), poly(alkyleneglyco)di-acrylate or methacrylate, cross-linking agent, a source of calcium ions, and water are described, as well as methods of their preparation and use.

85 Claims, 12 Drawing Sheets

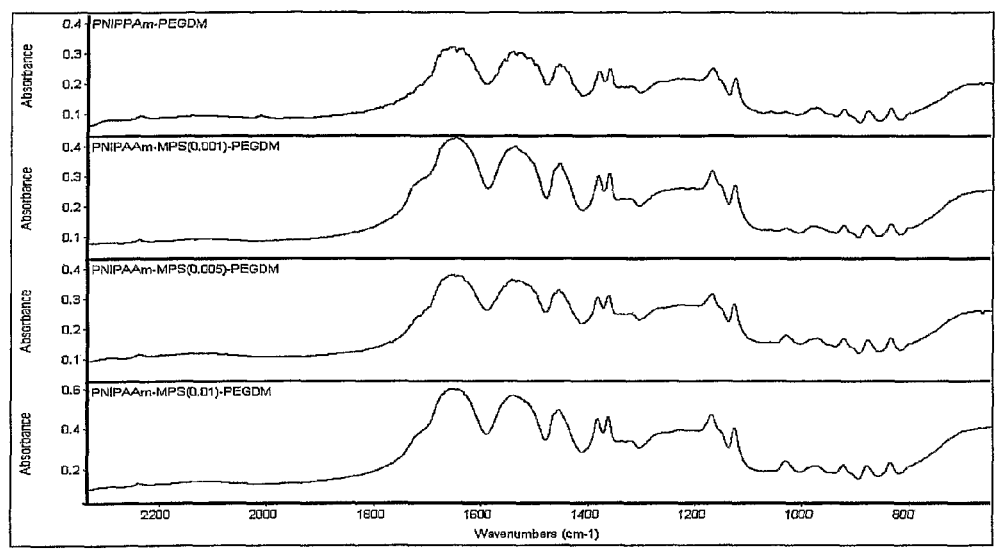
Figure 1: FTIR spectra of PNIPAAm-PEGDM with 0, 0.001, 0.005, and 0.01 mole MPS.

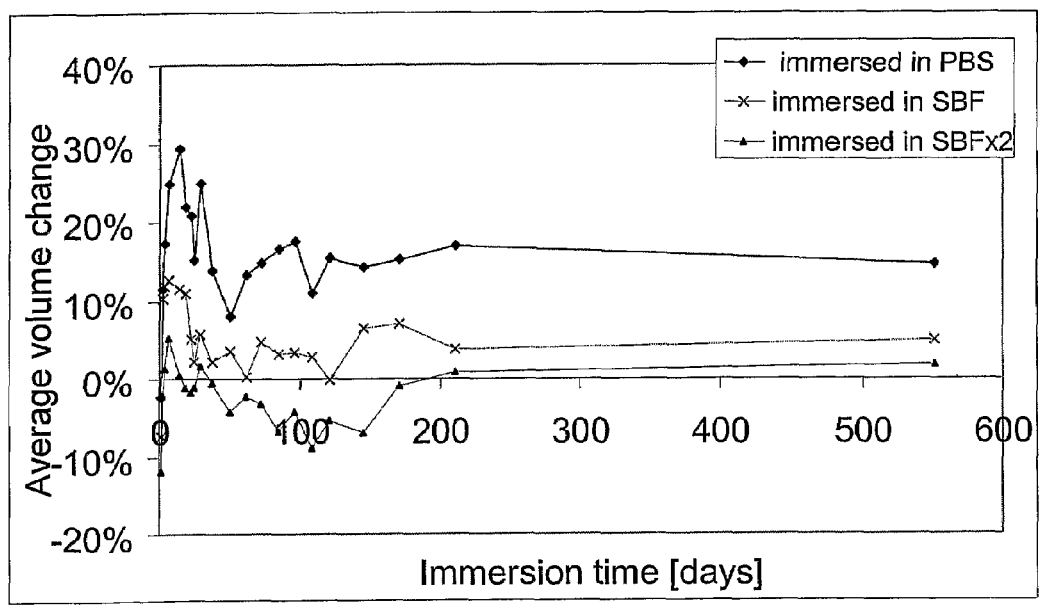
Figure 2A: Average volume change (n=3) of PNIPAAm-PEGDM after immersed in PBS, SBF and SBFx2 from 1 to 544 hours.

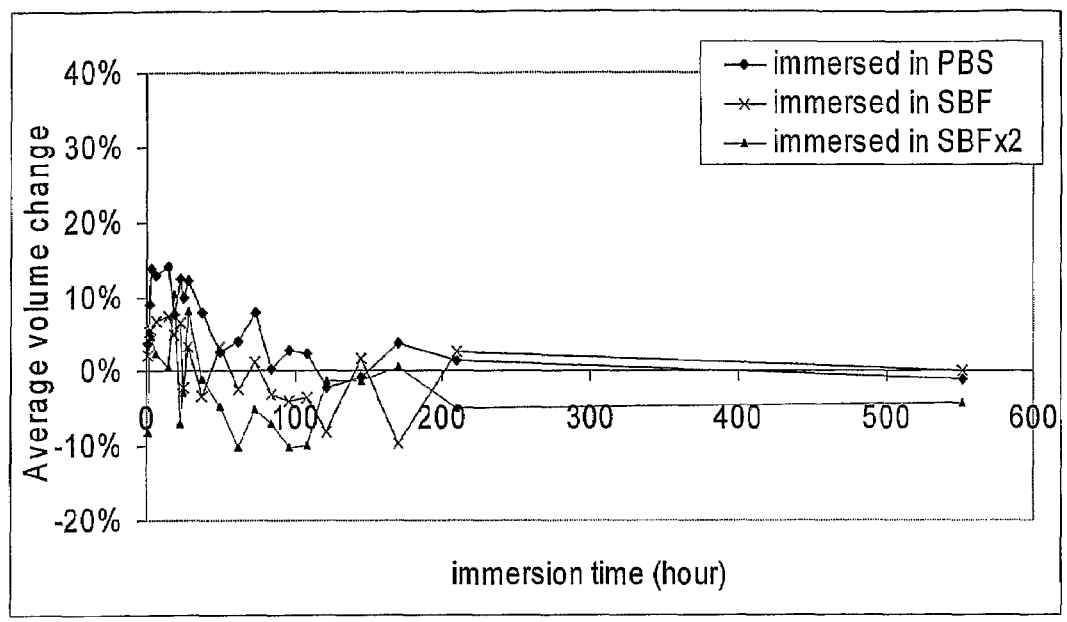
Figure 2B: Average volume change (n=3) of PNIPAAm-MPS (0.005 mole)-PEGDM after immersed in PBS, SBF and SBFx2 from 1 to 544 hours.

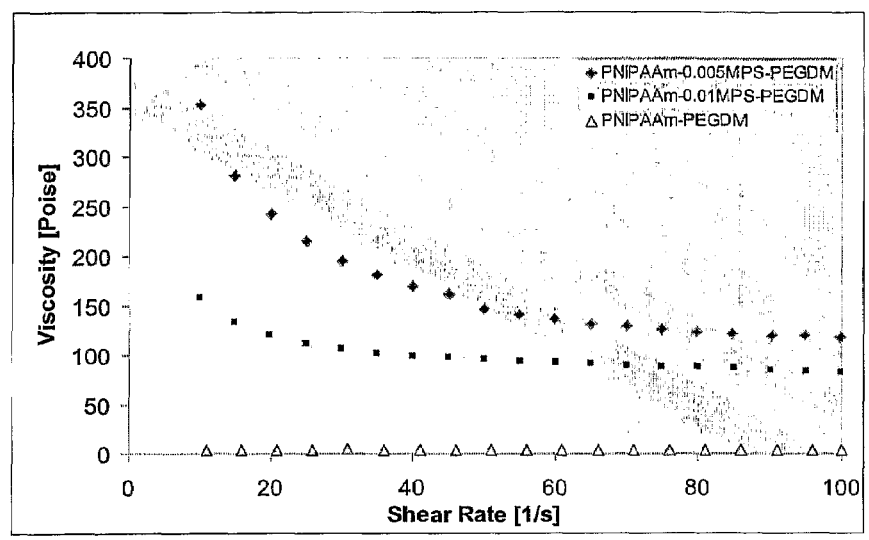
Figure 3A: Viscosity measurements of PNIPAAm-PEGDM with 0, 0.005 and 0.01 MPS molar ratio with respect to shear rate from 10 to 100s$^{-1}$.

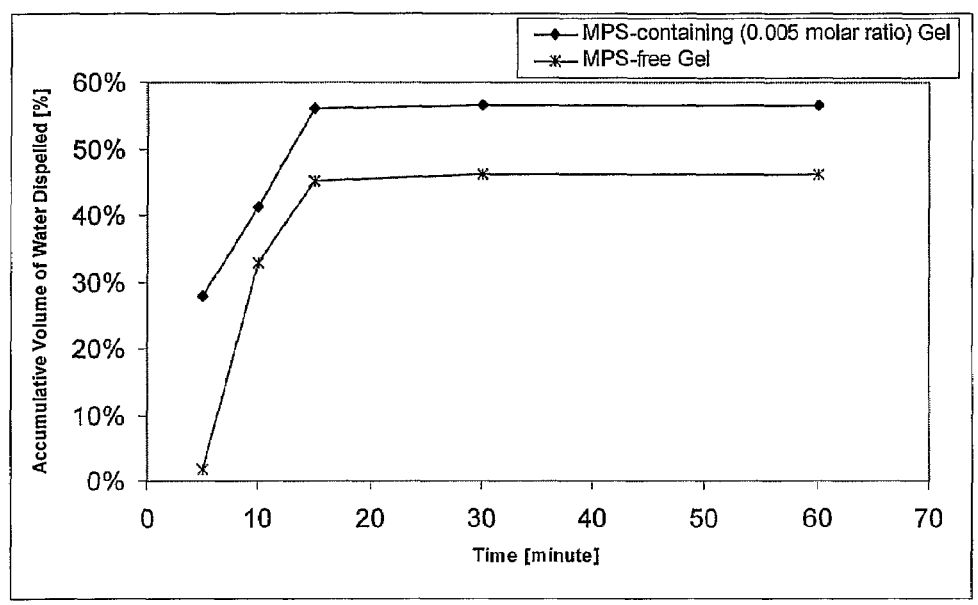
Figure 3B: The percentage of accumulative water dispelled volume during the initial 60 minutes of immersion in a 37 °C water bath.

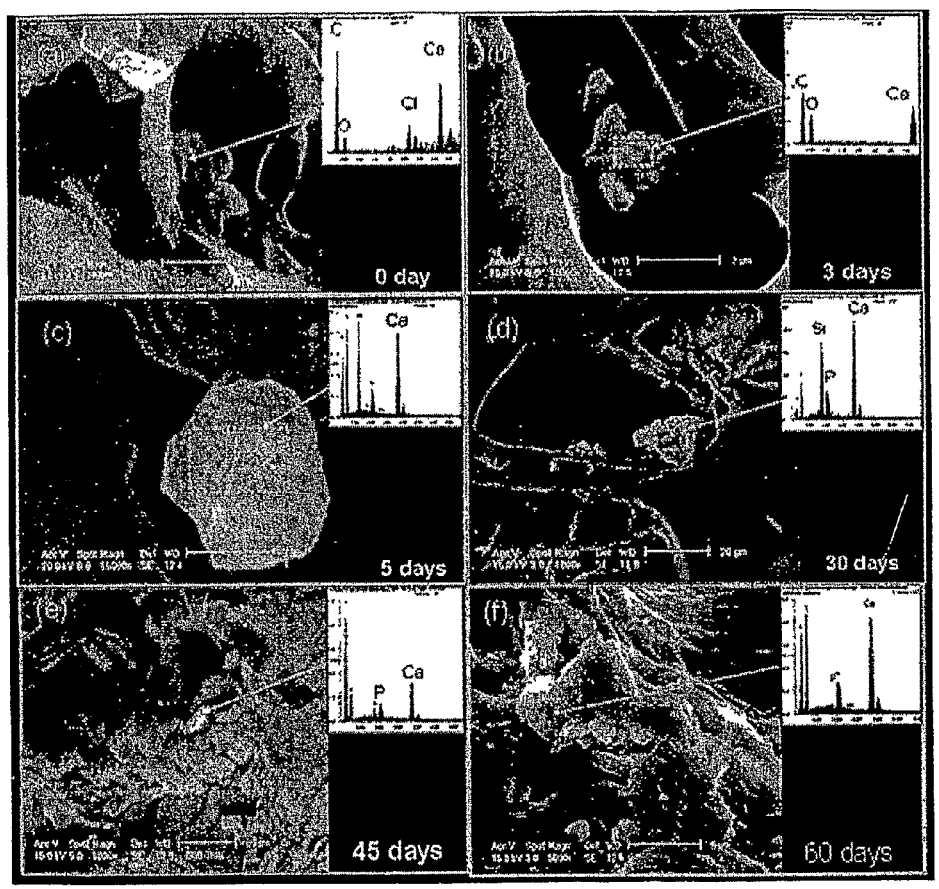
Figure 4: FE-SEM/EDX images of the bioactive nodules formed within the gel network (a) before immersion; (b) after 3 days; (c) after 5 days; (d) after 30 days; (e) after 45 days and (f) after 60 days immersion in SBF.

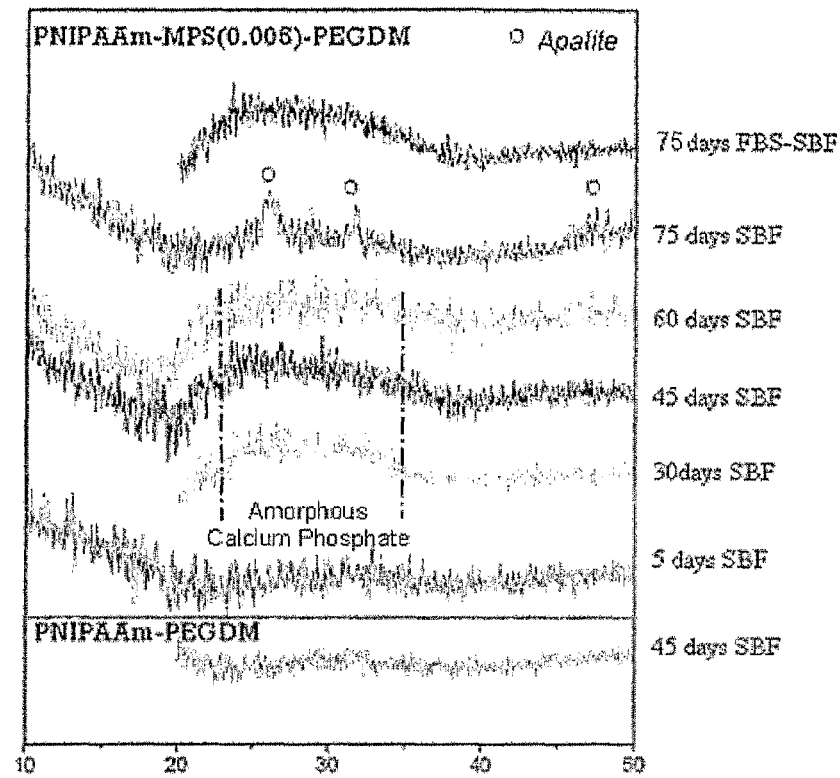
Figure 5: Normalized XRD spectra of SBF and FBS-SBF immersed PNIPAAm-PEGDM with and without 0.005 molar ratio MPS.

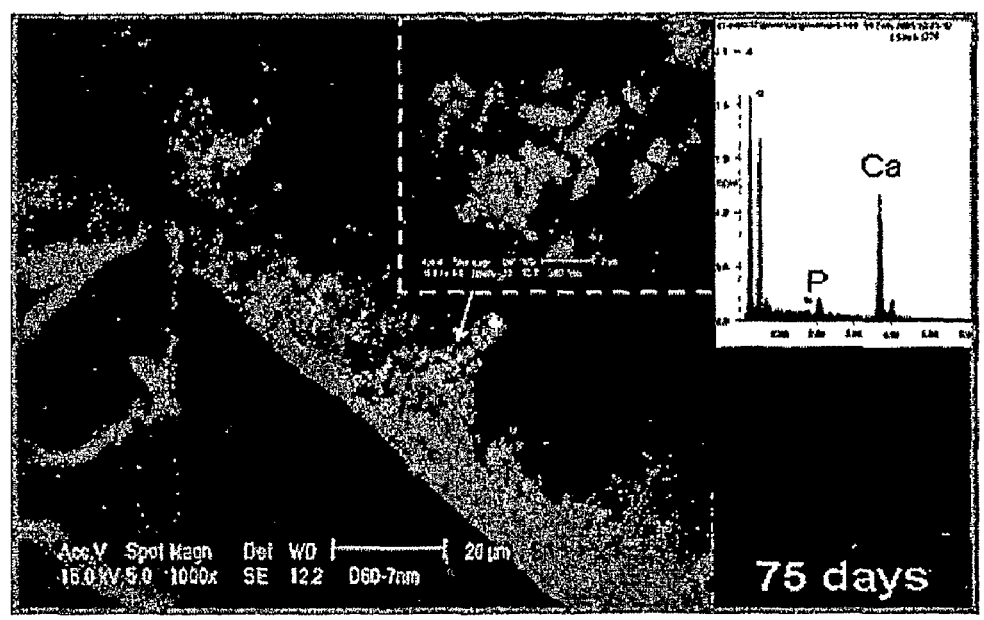
Figure 6: FE-SEM/EDX image of calcium phosphate crystals in the PNIPAAm-PEGDM meshwork after 75 days in SBF.

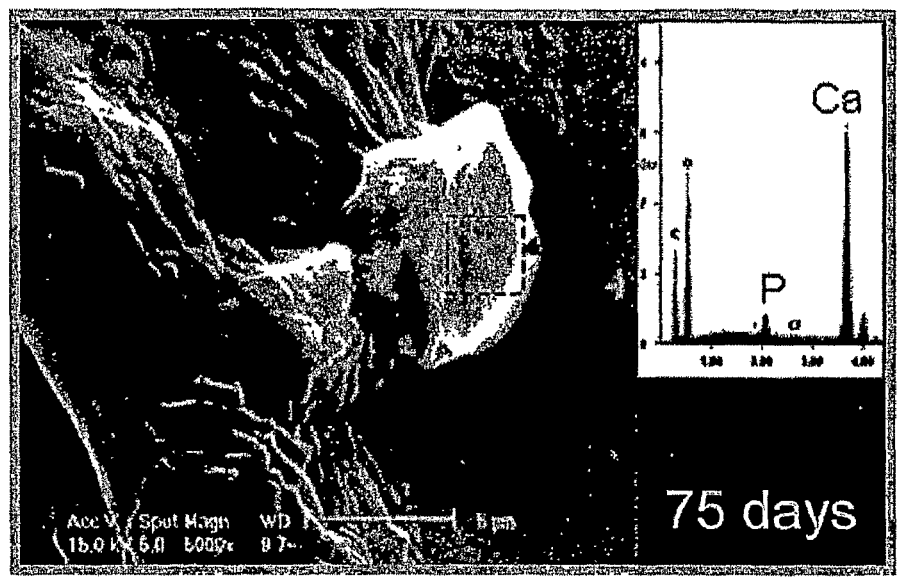
Figure 7: FE-SEM/EDX image of calcium phosphate in the PNIPAAm-PEGDM meshwork after 75 days in FBS-SBF.

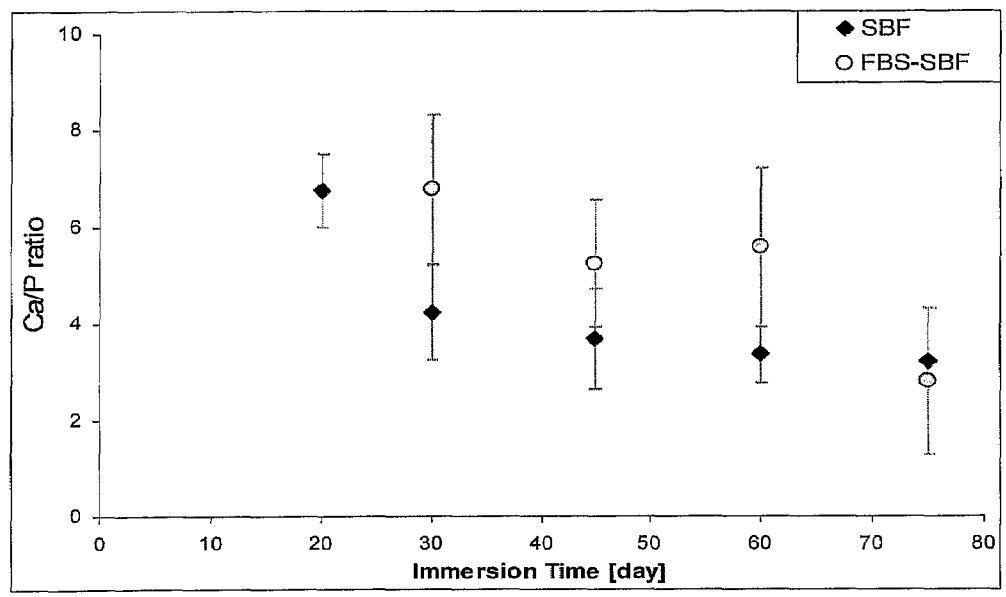
Figure 8: EDX data of the surface calcium (Ca) to phosphorous (P) ratios of the long term SBF and FBS-SBF immersed MPS-containing (0.005 molar ratio) gels.

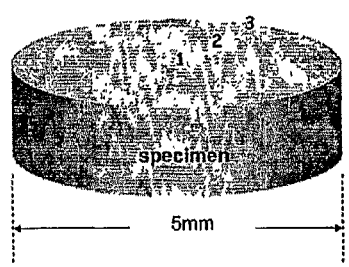
|  |  | 5 days immersed | | | 30 days immersed | | |
| --- | --- | --- | --- | --- | --- | --- | --- |
| No | Position | Chlorine | Carbon | Oxygen | Chlorine | Carbon | Oxygen |
| 1 | center | 0 | 91.23 | 8.77 | 1.03 | 88.56 | 10.41 |
| 2 | middle | 0.05 | 89.1 | 10.85 | 1.28 | 86.56 | 12.16 |
| 3 | surface | 0.22 | 90.21 | 9.57 | 1.47 | 89.45 | 9.08 |
Figure 9: The composition of chlorine, carbon and oxygen was measured on the cross-section of polymer ma3x of 5 and 30 days SBF immersed MPS-containing gels.

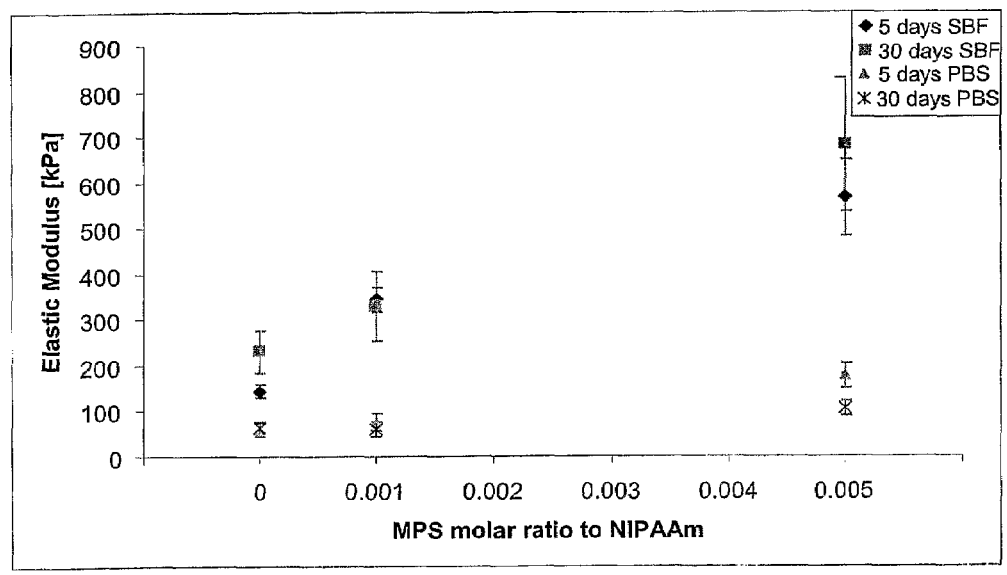
Figure 10: In vitro elastic modulus of PNIPAAm-PEGDM with various MPS molar ratio after 5 and 30 days immersion in PBS and SBF.

BIOACTIVE THERMOGELLING POLYMER SYSTEMS AND METHODS OF THEIR USE

CROSS-REFERENCE TO RELATED APPLICATIONS

This application is the National Stage of International Application No. PCT/US2006/012830 filed Apr. 7, 2006, which claims the benefit of U.S. Provisional Application No. 60/668,993, filed Apr. 7, 2005, the disclosure of which is incorporated herein by reference in its entirety.

FIELD OF THE INVENTION

The present invention relates to poly(N-alkylacrylamide)-based hydrogel polymer systems and methods of their use, for example, in bone fracture fixation, bone reinforcement, and bone resurfacing.

BACKGROUND OF THE INVENTION

Current options for alleviating pain due to vertebral fracture include vertebroplasty and kyphoplasty, which uses balloons inserted into the vertebral space to expand and compress the trabecular bone tissue to create a central cavity within the vertebra. Following cavity preparation, polymethylmethacrylate (PMMA), an acrylic bone cement, is injected into the cavity using percutaneous techniques. Typically, PMMA bone cement is used to restore the mechanical integrity of the vertebral body by stabilizing the trabecular fractures, thereby relieving pain.

One issue associated with vertebro- or kyphoplasty using PMMA cement includes the increased rigidity of the vertebral body in comparison to the superior and inferior vertebrae due to the modulus of the PMMA (1-3 GPa) as compared to trabecular bone tissue (0.05 GPa). This increased rigidity can lead to stress inconsistencies along the length of the spine and may lead to subsequent fractures. Indeed, subsequent facture has been reported in 26% of kyphoplasty cases. See Fribourg, D., et al., *Incidence of subsequent vertebral fracture after kyphoplasty*. The Spine Journal, 2003. 3(95S).

Moreover, while not frequently observed, pulmonary embolism leading to cardiac failure has been reported in patients receiving acrylic-based vertebroplasty, causing concern when the PMMA exits its intended locale. Hillmeier, J., P.-J. Meeder, and H. C. Kasperlk, The Spine Journal, 2003. 3(117S). Additionally, PMMA does not offer the advantage of osteoconductivity that is appreciated with calcium phosphate-based cements.

Because of the non-optimal properties associated with PMMA cements, certain alternative cementing materials have been investigated. Numerous groups have examined bioactive cements, either calcium phosphate cements or polymeric cements containing bioactive ceramics. While the bioactivity of these materials has been accepted as an improvement over PMMA, the mechanical properties of these cements have been questioned for sufficient fatigue strength and similarly high modulus mismatches to cancellous bone.

Recently, injectable bone substitutes combining polymers and bioactive ceramics have been described. One cement incorporated various bioactive glass beads and calcium phosphate granules to reinforce the polymer. While these composites provided better mechanical properties and higher bioactivity, some of the bioactive beads separated from the bone cement, leading to poor cement-bone interfacial properties. Lack of adhesion between the ceramic fillers and the polymer matrix is the major factor responsible for the filler-matrix debonding, ultimately resulting in a lower load carrying capacity of the cement. ((a) Kokubo, T., H.-M. Kim, and M. Kawashita, Biomaterials, 2003. 24(13): p. 2161-2175 (b) Rea, S. M., et al. Biomaterials, 2004. 25(18): p. 4503-4512 (c) Juhasz, J. A., et al. Biomaterials, 2004. 25(6): p. 949-955 (d) Kamitakahara, M., et al. Biomaterials, 2001. 22(23): p 3191-3196 (e) Ren, L., et al. Journal of Non-Crystalline Solids, 2001. 285(1-3): p. 116-122 (f) Kokubo, T., Acta Materialia, 1998. 46(7): p. 2519-2527).

Thus, there remains a need for injectable, bioactive materials having a compression modulus similar to that of vertebral trabecular bone tissue and having suitable material-bone interfacial properties.

SUMMARY OF THE INVENTION

Hydrogels comprising poly(N-alkylacrylamide), poly(alkyleneglycol)di-acrylate or methacrylate, cross-linking agent, a source of calcium ions, and water are described, as well as methods of their preparation and use. In preferred embodiments, the poly(N-alkylacrylamide) is poly(N-isopropylacrylamide). In other preferred embodiments, the poly(alkyleneglycol)di-acrylate or methacrylate is poly(ethyleneglycol)dimethacrylate. In other variants of the present invention, the source of calcium ions is calcium chloride. In others, the cross-linking agent is an-acrylo-siloxane.

Hydrogels of the present invention comprise physical properties that are useful in the area of bone fracture fixation, bone reinforcement, and bone resurfacing. For example, vertebral fractures may be repaired by injecting the hydrogels of the present invention into the vicinity of the fracture. Vertebral bone structures may be reinforced by injecting the hydrogels into the vicinity of the bone structures. Moreover, the hydrogels may be used to resurface articulating joints by providing the hydrogels to the joints.

BRIEF DESCRIPTION OF THE DRAWINGS

FIG. 1 depicts an FTIR spectra of hydrogels of the present invention comprising PNIPAAm-PEGDM with 0, 0.001, 0.005, and 0.01 mole MPS:NIPAAm.

FIG. 2A depicts an average volume change (n=3) of PNIPAAm-PEGDM after immersion in PBS, SBF and SBFx2 from 1 to 544 hours.

FIG. 2B depicts an average volume change (n=3) of PNIPAAm-MPS (0.005 mole)-PEGDM hydrogels of the present invention after immersion in PBS, SBF and SBFx2 from 1 to 544 hours.

FIG. 3A depicts viscosity measurements of hydrogels of the present invention comprising PNIPAAm-PEGDM with 0, 0.005 and 0.01 MPS molar ratio with respect to shear rate from 10 to 100 $s^{-1}$.

FIG. 3B depicts the percentage of accumulative water dispelled volume during the initial 60 minutes of immersion in a 37° C. water bath of hydrogels of the present invention and MPS-free gels.

FIG. 4 depicts FE-SEM/EDX images of bioactive nodules formed within gel networks of hydrogels of the present invention (a) before immersion; (b) after 3 days; (c) after 5 days; (d) after 30 days; (e) after 45 days and (f) after 60 days immersion in SBF.

FIG. 5 depicts a normalized XRD spectra of SBF and FBS-SBF immersed PNIPAAm-PEGDM with and without 0.005 molar ratio MPS.

FIG. 6 depicts an FE-SEM/EDX image of calcium phosphate crystals in PNIPAAm-PEGDM meshwork after 75 days in SBF.

FIG. 7 depicts an FE-SEM/EDX image of calcium phosphate in the PNIPAAm-PEGDM meshwork after 75 days in FBS-SBF.

FIG. 8 depicts EDX data of the surface calcium (Ca) to phosphorous (P) ratios of the long term SBF and FBS-SBF immersed MPS-containing (0.005 molar ratio) gels.

FIG. 9 depicts the composition of chlorine, carbon and oxygen was measured on the cross-section of polymer matrix of 5 and 30 days SBF immersed MPS-containing gels.

FIG. 10 depicts in vitro elastic moduli of PNIPAAm-PEGDM with various MPS molar ratios after 5 and 30 days immersion in PBS and SBF.

DETAILED DESCRIPTION OF ILLUSTRATIVE EMBODIMENTS

In accordance with the present invention, bioactive, injectable, hydrogel systems with tailorable mechanical properties are provided. The systems described herein facilitate the formation of calcium phosphate nucleation sites on and within a thermosensitive polymer, poly(N-alkylacrylamide)-co-poly(alkyleneglycol)di-acrylate or methacrylate, through incorporation of a cross-linking agent. These polymers are capable of liquid to solid phase transformation at about 32° C. With the presence of calcium phosphate sites, bone-like apatite can form on and within three-dimensional, structured organic hydrogel matrices at ambient temperatures and pressures using a short-term immersion process. Furthermore, these hydrogels demonstrate a lower degree of swelling with higher ionic content of the media, regardless of cross-linking agent concentration.

Hydrogels are three-dimensional hydrophilic polymer networks capable of imbibing large amounts of water or biological fluids and may show a swelling behavior depending on changes in the external environment. They can exhibit abrupt changes in their network structure swelling behavior, permeability, or mechanical strength in response to changes in pH, ionic strength, temperature, and electromagnetic radiation.

The hydrogels of the present invention comprise poly(N-alkylacrylamide). "Alkyl" as employed herein refers to both straight and branched chain radicals of up to 12 carbons, preferably 1 to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Poly(N-alkylacrylamides) of the present invention may exist as homopolymers or copolymers of N-alkylacrylamide polymers. In exemplary embodiments of the present invention, the poly(N-alkylacrylamide) is poly(N-isopropylacrylamide). Preferably, the poly(N-alkylacrylamide) has a lower critical solution temperature (LCST) of about between 29 and 36° C.

They hydrogels of the present invention also comprise a poly(alkyleneglycol)diacrylate or methacrylate. Poly(alkyleneglycol)di-acrylate or methacrylate is not generally thought to act as a cross-linking agent in the present invention. In preferred embodiments, the poly(alkyleneglycol)di-acrylate or methacrylate is poly(ethyleneglycol)dimethacrylate. In other embodiments, the poly(alkyleneglycol)di-acrylate or methacrylate is poly(propyleneglycol)dimethacrylate.

The hydrogels provided herein further comprise a source of calcium ions and a cross-linking agent. In additional embodiments of the present invention, the source of calcium ions is calcium chloride, calcium bromide, or calcium phosphate. Preferably, the source of calcium ions is calcium chloride. In preferred embodiments, the molar ratio of the source of calcium ions:cross-linking agent is about 1:1 to about 3:1.

Preferably, the molar ratio of the source of calcium ions: cross-linking agent is about 2:1.

As used herein, a "crosslinking agent" is a substance that promotes or regulates intermolecular covalent bonding between polymer chains. For example, the addition of at least one silane or/and siloxane may be favorable for forming such bonding. Suitable silanes include acyloxysilane, alkylsilane, alkyltrialkoxysilane, aminosilane, aminoalkylsilane, aminopropyltrialkoxysilane, bis-silylsilane, epoxysilane, fluoroalkylsilane, glycidoxysilane (such as, for example, glycidoxyalkyltrialkoxysilane), isocyanatosilane, mercaptosilane, (meth)acrylatosilane, monosilylsilane, multisilylsilane, bis(trialkoxysilylpropyl)amine, bis(trialkoxysilyl)ethane, sulfurous silane, bis(trialkoxysilyl)propyltetrasulfane, ureidosilanes (such as, for example, (ureidopropyltrialkoxy)silane) and vinylsilane (such as, vinyltrialkoxysilane and vinyltriacetoxysilane). Suitable siloxanes include those that correspond to the aforementioned silanes.

Other crosslinking agents include monoaldehydes (for example, formaldehyde, acetaldehyde, benzaldehyde, and the like), dialdehydes (such as glutaraldehyde, glyoxal, and succinic dialdehyde), trimethylol melamine, urea-formaldehydes, blocked aldehydes (Curesan™200 by BASF, for example), polyacrolein, boric acid and borates (such as borates, methyl borate, boron trifluoride, boric anhydride, pyroborates, peroxoborates and boranes). Other crosslinking agents include N-lactam carboxylates, dicarboxylic acids (maleic acid or oxalic acid), di-isocyanates, divinyl sulphate, and inorganic compounds such as germanic acids and germanates, titanium salts and esters, chromates and vanadates, cupric salts and other Group IB salts. In exemplary embodiments, the cross-linking agent is an acrylo-siloxane. In other embodiments, the cross-linking agent is an acryloxy- or methacryloxyalkylpolyalkoxysilane. Preferably, the cross-linking agent is 3-methacryloxypropyltrimethoxysilane (MPS).

Modifications can be made to the hydrogen systems of the present invention to further modify mechanical stiffness. In some embodiments, methyl methacrylate, poly(methyl methacrylate), vinyl acetate, poly(vinyl acetate), or mixtures thereof, can be added to the hydrogel polymer systems of the present invention. The addition of these materials may increase the compression moduli of the hydrogel systems of the present invention. Methyl methacrylate, poly(methyl methacrylate), vinyl acetate, poly(vinyl acetate), or mixtures thereof may be present in amounts up to about 25% by weight.

In other embodiments, hydrogels of the present invention may further comprise at least one calcium-binding component. These components could increase the bioactivity of the hydrogels of the present invention. Such calcium-binding components may include, for example, carboxylic acids, such as acrylic acid, poly(acrylic acid), methacrylic acid, poly (methacrylic acid), or mixtures thereof. These components may be present in hydrogels of the present invention in amounts up to about 10% by weight.

Hydrogels of the present invention may include homopolymers, copolymers, or mixtures thereof. The hydrogels of the present invention may be prepared by employing the following process, for example. Nitrogen gas can be bubbled through a mixture of purified N-alkylacrylamide and poly(alkyleneglycol)di-acrylate or methacrylate in a solvent such as methanol. In preferred embodiments, the N-alkylacrylamide is N-isopropylacrylamide (NIPAAm) and the poly (alkyleneglycol)di-acrylate or methacrylate is poly(ethyleneglycol)dimethacrylate (PEGDM). Preferably, the N-alkylacrylamide and the poly(alkyleneglycol)di-acrylate or methacrylate are present in about a 250:1 to about a 150:1 weight ratio, preferably being a 200:1 weight ratio, representing about 0.05 mol % of poly(alkyleneglycol)di-acrylate or methacrylate.

In some embodiments, the amount of cross-linking agent added can be in an amount up to about a molar ratio of 0.01 cross-linking agent:N-alkylacrylamide. In other embodiments, the cross-linking agent:N-alkylacrylamide molar ratio is between about 0.0005 and 0.01. In others, the cross-linking agent:N-alkylacrylamide molar ratio is about 0.0005. In yet others, the cross-linking agent:N-alkylacrylamide molar ratio is about 0.0075. Preferably, the cross-linking agent:N-alkylacrylamide molar ratio is about 0.005. In further embodiments, the cross-linking agent:N-alkylacrylamide molar ratio is about 0.003 or 0.001. Preferably, the cross-linking agent is an acrylo-siloxane. In other embodiments, the cross-linking agent is an acryloxy- or methacryloxyalkylpolyalkoxysilane. More preferably, the cross-linking agent is 3-methacryloxypropyltrimethoxysilane.

An initiator is added to the mixture and the mixture is polymerized. One preferred initiator is 2,2-azobisisobutyronitrile (AIBN). Preferably, the mixture is polymerized at 65° C. for either 6 or 48 hours and stirred. In some embodiments, the polymerized mixture is stirred overnight.

The polymer can be dried in a vacuum oven and the dried polymer can be pulverized to a powder. A solution of the polymer can be prepared by addition of water. In preferred embodiments, the polymer solution may contain about 65-85 wt % of water. In more preferred embodiments, the polymer solution is 25 wt % polymer and 75 wt % deionized water.

The hydrogels of the present invention may be used for the fixation of hard tissue, for example, in vertebroplasty or kyphoplasty. In some embodiments, the hydrogels of the present invention may be injected within a vertebral space so as to restore the mechanical integrity of fractured, or otherwise weakened, vertebra, using techniques known in the art, for example, by injecting the hydrogels into the vicinity of the fracture. Additionally, the hydrogels may be injected within vertebral bone tissue so as to reinforce those bones having a risk for fracture, for example, in osteoporotic, osteopenic, trauma, or tumor patients. For example, vertebral bone structures can be reinforced by injecting the hydrogels into the vicinity of the bone structures. These hydrogels may also have general orthopaedic applications. For example, the hydrogels may be used for joint resurfacing, wherein the hydrogel is injected into an articulating joint to provide a bearing surface that can bond to underlying bone tissue. Knee joints may be resurfaced using the hydrogels of the invention, for example.

In other embodiments, the hydrogels of the present invention may be used in addition to materials such as PMMA, that are used in vertebroplasty or kyphoplasty procedures. For example, it is envisioned that PMMA could be used as it is currently employed in such procedures, and that the hydrogels described herein could be injected into the intra-trabecular regions surrounding the PMMA material. Such a use would provide reduced stress concentration to the surrounding tissues by providing more of a modulus translation between the PMMA and the adjacent tissues, for example end plates, intervertebral discs, and adjacent vertebrae. Such embodiments may limit stress risers that have been implemented in adjacent-level fractures. The hydrogels may further comprise medicaments, osteoclastic inhibitors, pain relievers, chemotherapeutic agents, or mixtures thereof, for delivery to a patient in need of such agents.

The hydrogels may also comprise imaging materials, for example, radiopacifiers, radiomarkers, or radiopaque materials so that they may be visualized using techniques known in the art. Such materials include barium sulfate, iodine, and heavy metal powders. It may also be desirable that the hydrogels of the present invention further comprise medicaments, osetoelastic inhibitors, pain relievers, chemotherapeutic agents, mixtures thereof, and the like, for delivery to a patient in need of such agents.

The hydrogels of the present invention preferably have elastic moduli that are useful in hard tissue applications. Preferably, hydrogels of the present invention have elastic moduli of about 0.5-0.9 MPa. With the addition of 0.005 molar ratio of MPS, the in vitro elastic modulus of the PNIPAAm-PEGDM-$CaCl_2$-based polymer was determined to be 0.7 MPa, representing about a 200% increase from MPS-free system, which has a reported elastic modulus of about 0.244 MPa. (FIG. 10) (See Ohya, S., S. Kidoald, and T. Matsuda, Biomaterials, 2005. 26(16): p. 3105-3111.).

As depicted in FIG. 10, differences in elastic moduli were more pronounced in the presence of simulated body fluid (SBF). As compared to phosphate buffered saline (PBS), immersion of the gels of the present invention in SBF served to enhance the bioactivity reactions, as well as increase the mechanical properties, even after 30 days of immersion in vitro. The SBF-immersed gels likely exhibited more cross-linking from the higher ion concentration of SBF than the PBS immersed ones. Generally, an increase in ion concentration enhances the compression moduli of the hydrogels of the present invention. With a higher degree of cross-linking, further increases in elastic modulus would likely result.

With the addition of a cross-linking agent and a source of calcium ions, poly(N-alkylacrylamide)-based hydrogels become bioactive gels. FE-SEM images and EDX spectra of the MPS-containing gels showed bioactive sites were nucleated locally and grew three-dimensionally into calcium phosphate nodules after 30 days of immersion in SBF at 37° C. FIG. 4 show that the bioactive sites were embedded in the polymer matrices. In comparing the FE-SEM images of 0, 3, and 5 days-SBF-immersed gel with the images of 30, 45, and 60 days-SBF-immersed gels, an increase in the number of bioactive sites within the polymer matrices is observed (FIG. 4).

Based on the FE-SEM images and EDX spectra, the nucleation and growth of calcium-phosphate were observed in the PNIPAAm-0.005 molar ratio MPS-PEGDM matrices of 30 days-SBF and FBS-SBF-immersed specimens (See FIG. 4, for example). The XRD spectra revealed that these bioactive sites were amorphous even after 30 days immersed in SBF, as shown in FIG. 5. These amorphous calcium phosphates have insignificant influence on the mechanical properties of the gels. After 75 days immersion, the amorphous calcium phosphate grew into apatite crystals. (See FIGS. 6 and 7). As a substantial amount of apatite forms within the polymer and leads to direct bone bonding, the global mechanical properties of the gel are expected to be improved. Also, the calcium to phosphorus ratio of the bioactive element is slowly reduced and tends to approach the 1.55 to 2.2 range, signifying hydroxyapatite, the primary inorganic component of bone. (See FIG. 8) (Katz, J., *Composite Materials Models for Cortical Bone, in Mechanical Properties of Bone*, S. Cowin, Editor. 1981, Ed. A.S.M.E.: NY. p. 171-184.). The presence of chlorine ions throughout the gels' thickness of the 30 day SBF-immersed samples appeared to have negligible influence on the mechanical properties of the systems (FIG. 9).

Nucleation and growth of apatite are controlled by specific interactions between the calcium and phosphate ions and protein. (Combes, C. and C. Rey, Biomaterials, 2002. 23(13): p. 2817-2823.). The adsorption of proteins on the mineral surface can alter the nucleation and crystallization rate of apatite. (El-Ghannam, A., Journal of Biomedical Materials Research, 2004. 169A(3): p. 490-501.). In the hydrogels of the present invention, apatite formation in the MPS-containing gel was observed after 75 days of SBF immersion. The proliferation, crystallization, and phosphate uptake of the nodules in the FBS-SBF immersed gels were slower than those in the SBF, as shown in FE-SEM/EDX images and calcium to phosphorous ratios. (See FIGS. 4 and 6-8).

Polymer solutions prepared in accordance with the present invention, comprising molar ratios of up to 0.01 of cross-linking agent:N-alkylacrylamide, transformed to film gels at about 32.6° C. (the lower critical solution temperature, "LCST"). Ease of injection through a 20 gauge needle was accomplished with MPS concentrations of approximately 0.01 molar ratio or less. The gel becomes solid instantaneously in 37° C. SBF. Hydrogels prepared according to the present invention have equilibrium viscosities of about 75-125 Poise. In preferred embodiments, the equilibrium viscosity is about 115-125 Poise. In other embodiments, the equilibrium viscosity is about 75-90 Poise. The viscosity measurements ($\eta$) of the polymer solutions comprising 0, 0.005, and 0.01 molar ratio of MPS with respect to shear rate of 10 to 100 $s^{-1}$ are plotted in FIG. 3A. The room temperature-measured viscosity of the polymer solutions reduced with increasing shear rate and reached an equilibrium level at 80 $s^{-1}$ shear rate. The equilibrium viscosity of 25 wt % PNIPAAm-PEGDM in DI water with 0, 0.005, and 0.01 molar ratio MPS content, at a shear rate of 100 $s^{-1}$, was determined to be 3, 118 and 83 Poise, respectively.

When gels were heated to 37° C., they became opaque and pliable in SBF, but once immersed in SBF for 24 hours, the hydrogels turn transparent and more rigid. During the rapid phase transition at 37° C., the hydrogels dramatically collapse and release a large fraction of pore water within the first hour of heating. The specimens then tend to swell (increase in volume) and reach equilibrium (volume change within 10%).

Polymer solutions prepared in accordance with the present invention complete phase transformation to a firm gel within 3 minutes in a 37° C. water bath. The percentage of accumulative volume of the water dispelled from phase-transformed gels as a function of immersion time is plotted in FIG. 3B. The accumulative volume of water dispelled becomes steady and no significant additional volume of water dispelled from the gels is detected after 15 minutes of immersion. The MPS-containing gels showed a higher volume of dispelled water than the MPS-free gel, but both specimens demonstrated a rapid polymer setting and reached a stable volume within a relatively short period of time after immersion. For the compositional ranges examined, no significant influence was observed with MPS and PEGDM content on the phase transition behavior and LSCT of the hydrogels. The instantaneous phase transition and rapid dehydration of the gels at 37° C. in SBF is beneficial for hard tissue replacements because it offers a physically stabilized material in the body within the first hour of surgery, tending to reduce the overall surgical risk, since it can be injected into a surgical site in a minimally invasive manner.

Those of skill in the art will appreciate that numerous changes and modifications may be made to the embodiments and examples described herein and that such changes and modification may be made without departing from the spirit of the invention.

EXAMPLES

Example 1

Preparation of Polymer Systems

Nitrogen gas was bubbled through a mixture of purified N-isopropylacrylamide (NIPAAm) and poly(ethyleneglycol) dimethacrylate (PEGDM) in 200:1 weight ratios (about 0.05 mol % of PEGDM) in methanol solvent. Poly(N-isopropylacrylamide) (PNIPAAm) is a thermosensitive hydrogel having a lower critical solution temperature (LCST) between 29 and 36° C. in aqueous solution. As a result, PNIPAAm is soluble in water at room temperature, but insoluble at physiological temperature. Various molar ratios of 3-methacryloxypropyltrimethoxysilane (MPS) to NIPAAm (0 to 0.01) and a constant molar ratio of calcium chloride:MPS (2:1) was added to the polymer mixture with the initiator 2,2-azobisisobutyroni3le (AIBN). The mixture was polymerized at 65° C. for either 6 or 48 hours, and was stirred overnight at room temperature. The polymer was dried for a few days in a vacuum oven to further remove the solvent, and then the dried PNIPAAm-MPS-PEGDM-$CaCl_2$ was ground to fine powder. Polymer solution was prepared with 25 wt % polymer and 75 wt % deionized (DI) water at room temperature.

Example 2

Polymer System Characterization

After synthesis, the polymers with various MPS contents were characterized using fourier transform infrared spectroscopy (FTIR; Magna-IR 560, Nicolet, Madison, Wis.) and a field emission environmental scanning electron microscope (FE-SEM), equipped with Electron-Dispersive Spectroscopy (EDS; Philips XL 30, Netherlands), at $1.4 \times 10^{-9}$ mtorr vacuum level and 15 keV voltage. The polymer powders were dissolved in acetone for FTIR analysis. Prior to FE-SEM/EDS determination, the polymers were coated with platinum with a platinum sputter for 60 seconds.

FIG. 1 shows the FTIR spectra of the gels with different chemis3es. Comparing the FTIR spectra of MPS-free gels to MPS-containing gels, the peak at 1030 $cm^{-1}$ (Si—O groups) appeared only in the materials with 0.005 and 0.01 molar ratio of MPS. The 0.001 molar ratio MPS content in the gel was not detectable likely due to the FTIR sensitivity limit (±1%). The Si—O groups were detected for the 0.005 and 0.01 MPS molar ratio.

Example 3

LCST Determination

The LCST of the polymer solution (25 wt % of polymer in DI water) was evaluated using differential scanning calorimetry (DSC; DSC 2010, TA Instruments, New Castle, Del.) as a function of MPS content. The samples were heated at 1° C./min to 50° C. under nitrogen gas purge. Once a plot of heat flow vs. temperature was obtained, the LCST was determined to be the temperature at the minimum heat flow point of the curve.

Example 4

Change in Volume Estimation

Firm hydrogels were prepared by molding the polymer solution at 37° C. The hydrogels were immersed in phosphate buffered solution (PBS), simulated body fluid (SBF), or double ion concentrated SBF (SBFx2) from 1 to 544 hours. In the preparation of PBS, 9.6 g of Dulbecco's PBS powder (Sigma-Aldrich Co., St. Louis, Mo.) was dissolved in DI water, the ion concentration of PBS is listed below in Table 1. For the preparation of SBF and SBFx2, various chemicals (as provided in Table 1) were dissolved in 1.0 mM 3 s-HCl (Sigma-Aldrich Co., St. Louis, Mo.) and buffered to pH 7.6 at 37° C. The temperature of the solutions was maintained at 37° C. The volume charge of the hydrogels after immersion in PBS, SBF, or SBFx2 was calculated by subtracting the gel volume at 37° C. after one hour of immersion from the gel volume after various immersion hours. The average volume change is determined based on the volume change of three specimens.

TABLE 1

Ion composition and concentration of three biological medias: PBS, SBF and SBFx2.

| Ion | Concentration in PBS [mmol] | Concentration in SBF [mmol] | Concentration in SBFx2 [mmol] |
|---|---|---|---|
| $Na^+$ | 6.95 | 152 | 304 |
| $Cl^-$ | 1.55 | 135 | 270 |
| $K^+$ | 1.5 | 5 | 10 |
| $H_2PO_4^-$ | 4.21 | 1.0 | 2.0 |
| $Mg^{+2}$ | — | 1.5 | 3 |
| $HCO_3^-$ | — | 27 | 54 |
| $SO_4^{-2}$ | — | 0.527 | 1.054 |
| $Ca^{+2}$ | — | 2.5 | 5 |

Example 5

Bioactivity Characterization

The effect of protein adsorption on the bioactivity of PNIPAAm-MPS (0.005 mole)-PEGDM specimens was analyzed using a biological media containing protein, 10 vol % fetal bovine serum (FBS; Biomeda Co., Foster City, Calif.)-90 vol % simulated body fluid (SBF). The 37° C.-formed, 0.005 mole MPS-containing gels (cylindrical specimens with an average 5 mm diameter and 7 mm height) were immersed in 5 ml of 37° C. biological fluids, SBF and FBS-SBF, for the in vitro formation of the apatite within the bioactive polymer network. The solutions were renewed every 30 days. After soaking for a given period, the specimens were removed from the solution, ultrasonically washed with 37° C. deionized water for 30 minutes, and then vacuum dried at room temperature.

The formation of tissue bonding is known through the development of an apatite layer in vitro, where an apatite layer with a calcium-to-phosphorous ratio higher than 1.4 is known to promote direct tissue bonding. (Hench, L. L., *Bioceramics*. Journal of the American Ceramic Society, 1998. 81: p. 1705-28.). The presence of calcium and phosphate after immersion in SBF was examined using FE-SEM/EDX (Philips XL 30, Netherlands) and FTIR (Magna-IR, Nicolet, Madison, Wis.), respectively. The apatite formation within the polymer after long term immersion (30, 45, 60, 75 and 90 days) in SBF was verified by powder X-ray diffractometry (XRD: Rigaku X-ray diffractometer, Rigaku/USA Inc., Danvers, Mass., USA). The calcium to phosphorus atomic ratios of 5 bioactive nodules within the polymer ma3x were also calculated using EDS after immersion in SBF and FBS-SBF from 30 to 75 days. Further, the chlorine adsorption of the 5 and 30 days SBF immersed polymer ma3x was determined by quantifying the chlorine, carbon and oxygen composition across the gel thickness.

Example 6

Initial Phase Transformation

The phase transformation behavior of PNIPAAm-PEGDM hydrogels with and without 0.05 mol % MPS during the initial 60 minutes was analyzed. The polymer solution was injected in a 30° C. pre-heated 10 mm diameter glass container and placed in a 37° C. water bath for complete phase transformation. The accumulative volume of water dispelled from the polymer solution after phase transformation was measured. The dispelled water volume was determined through extracting the water from the gel contained glass container after 1, 5, 15, 30 and 60 minutes of phase transformation.

Example 7

Injectability and Viscosity Studies

An injection process can be considered in two physical processes: (1) delivery of the injected materials in the implantation site, and (2) infiltration of the injected materials with the existing biological environment. The delivery of the hydrogels was examined qualitatively via the injection of polymer solutions with various MPS molar ratios through a 20 gauge needle in 37° C. SBF manually with a moderate force. The in situ infiltration properties of the bioactive hydrogel were studied via the viscosity measurement of the polymer solution as a function of MPS molar ratio. The viscosity measurement of three polymer solution (25 wt % of PNIAAm-PEGDM with either 0, 0.005, or 0.01 MPS molar ratio in deionized water) was performed using a dynamic stress rheometer (DSR; DSR-200 Rheometics, TA Instruments, New Castle, Del.) with the cone/plate test setup at room temperature. The applied shear rate was 1 to 100 s-1 for all specimens.

Example 8

In Vitro Compression Test

The polymer solution (see Example 1) was poured into a 10 mm diameter polymer cylinder and the mold was heated to 37° C. for phase transformation. The firm gels were the stored in 37° C. immersion media (phosphate buffered saline, PBS, and simulated body fluid, SBF) for 5 days to reach the equilibrium state. In the preparation of PBS, 9.6 g of Dulbecco's PBS powder (Sigma-Aldrich Co., St. Louis, Mo.) was dissolved in DI water. The simulated body fluid (SBF) contains ions to represent the ionic concentrations of plasma: 2.6 mM $Ca^{2+}$ as $CaCl_2$, 1 mM $HPO_4^{2-}$ as $K_2HPO_4.3H_2O$, 152 mM $Na^+$ as NaCl, 135 mM $Cl^{2+}$ as $CaCl_2$, 5 mM $K^+$ as KCl, 1.5 mM $Mg^{2+}$ as $MgCl_2.6H_2O$, 27 mM $HCO^{3-}$ as $NaHCO_3$, and 0.5 mM $SO_4^{2-}$ as $MgSO_4.7H_2O$. The chemicals were dissolved in deionized water and buffered to pH 7.6 at 37° C. with 1.0 mM 3 s-HCl (Sigma, St. Louis, Mo.). (Yao, J., et al., *The effect of bioactive glass content on synthesis and bioactivity of composite poly (lactic-co-glycolic acid)/bioactive glass substrate for tissue engineering*. Biomaterials, 2005. 26(14): p. 1935-1943; Marcolongo, M., et al., *Bioactive glass fiber/polymeric composites bond to bone tissue*. Journal of Biomedical Materials Research, 1998(39): p. 161-170.). The total ion concentration of SBF is higher than that in PBS.

After the gel stabilized with the immersion solution, the effect of volume change of the gels on its mechanical properties would be negligible. The specimens were tested in unconfined compression using a mechanical testing system (Instron Model 4442, Instron Co., Park Ridge, Ill.) fitted with a 50N load cell and 37° C. immersion bath with either PBS or SBF. Specimens were compressed at a strain rate of 100% strain per minute. Load and displacement data was recorded at 20 points per second with the Instron Series IX software. This data was converted to stress and strain values in Microsoft Excel using the specimen's initial dimensions. A compressive elastic modulus was measured as the initial linear slope of the stress-strain response at 0.05 mm/mm strain. One-way ANOVA analyses were performed for compressive modulus results at 0.05 level of significance.

Example 9

In Vitro Physical Properties

The average volume change (n=3) of PNIPAAm-PEGDM with 0 and 0.005 molar ratio of MPS, immersed in three biological media: PBS, SBF and SBFx2, was examined from 1 to 544 hours (FIGS. 2A and 2B). As shown in Table 1 supra, PBS has lower ion concentrations than SBF and SBFx2 has the greatest ion content among the three immersion media. The average volume change of gel with or without MPS appeared to vary with the ion content of the media. FIGS. 2A and 2B show that the PBS immersed gels showed higher average volume change than SBF or SBFx2 immersed gels during the initial 4 days immersion.

Samples with 0.005 MPS molar ratio exhibited less average volume change than those without MPS. The maximum average volume change of 14% of the MPS-containing gel was measured after 6 and 14 hours immersion in PBS, while the maximum reading of 29% was measured after 14 hours immersion in PBS. In brief, the in vitro bioactive hydrogel showed less average volume change with increased ion concentration of the simulated body fluid. After 5 days of immersion, the average volume change of all MPS containing hydrogel specimens became stable (within 10%) in all simulated biological conditions.

Example 10

Surface Reaction Kinetics

The XRD spectra were normalized with the unimmersed specimens accordingly. FIG. 5 demonstrates the normalized XRD spectra of the MPS-free gels after 45 days-SFB immersion and MPS-containing gels after 5, 30, 45, 60 and 75 days-SBF immersion and 45 days-FBS-SBF immersion. No indication of calcium phosphate formation was revealed in the XRD spectra of the 45 days SBF immersed MPS-free gel. The MPS-containing gels showed changes in the XRD pattern as immersion times changed from 5 to 75 days immersion in SBF. The differences in the XRD patterns between 5 days immersed bioactive specimen and the 30, 45 and 60 days SBF immersed MPS-containing specimens indicate the formation of amorphous calcium phosphate (FIG. 5). After 75 days immersion in SBF, the XRD peaks assignable to apatite were observed. (See Kokubo, T., H.-M. Kim, and M. Kawashita, *Novel bioactive materials with different mechanical properties*. Biomaterials, 2003. 24(13): p. 2161-2175.). The FE-SEM/EDX results of these specimens (FIG. 6) illustrated calcium phosphate crystals were formed on the surface of the polymer. But the XRD spectra and FE-SEM image of the 75 days FBS-SBF immersed gels showed no apatite formation (FIGS. 5 and 7).

The initial detection of phosphorous in the bioactive sites of the SBF immersed gels was shown after 20 days immersion, but it was 10 days delayed for the FBS-SBF immersed specimens (FIG. 8). Once the calcium phosphate formed in the FBS-SBF gels, its phosphorous content increased in a faster pace than the ones of SBF immersed; and after 75 days, no statistical differences were detected in the calcium to phosphorous ratios in the bioactive sites between the two specimens. The FE-SEM/EDX results of the unimmersed specimens (FIG. 4) showed the calcium chloride containing bioactive nodule was embedded in the polymer ma3x. Phosphorus from the surrounding fluid was gradually reacted with the calcium rich bioactive nodules and led to calcium phosphate formation. The chlorine, carbon and oxygen composition across the gel thickness were varied between 5 and 30 days SBF immersed specimens. FIG. 9 demonstrates that chlorine was not detectable at the center of 5 days SBF-immersed specimens, while about 1 mol % of chlorine was detected across the 30 days SBF-immersed gel thickness.

Example 11

In Vitro Mechanical Properties

FIG. 10 shows the in vitro elastic modulus of 30 day-PBS- and SBF-immersed PNIPAAm-PEGDM while 0, 0.001, and 0.005 molar ratios of MPS exhibited no significant differences from the 5 day immersed samples. The 30 days immersed MPS-free and 0.005 molar ratio MPS-containing specimens demonstrated higher elastic modulus after immersion in SBF than those immersed in PBS (259% and 554% more respectively). With the addition of 0.005 MPS-molar ratio, the elastic modulus of the 30 day PBS immersed firm gel had a 60% increase, reaching 0.1 MPa, while the 30 day SBF immersed samples had almost a two-fold increase to about 0.7 MPa.

After immersion in PBS for 30 days, the elastic modulus of 0.005 molar ratio MPS-containing gel was significantly decreased (41%, p=0.001) in comparison to those of 5 day immersion. Nevertheless, the elastic moduli of 30 day SBF immersion gels have no significant difference in comparison to those of the corresponding 5 day.

The invention claimed is:
1. A hydrogel comprising:
poly(N-alkylacrylamide),
poly(alkyleneglycol)di-acrylate or poly(alkyleneglycol) di-methacrylate,
cross-linking agent,
a source of calcium ions, and
water.
2. A hydrogel according to claim 1 wherein the poly(N-alkylacrylamide) is poly(N-isopropylacrylamide).
3. A hydrogel according to claim 1 wherein the poly(alkyleneglycol)di-acrylate or poly(alkyleneglycol)di-methacrylate is poly(ethyleneglycol)dimethacrylate or poly(propyleneglycol)dimethacrylate.
4. A hydrogel according to claim 1 wherein the cross-linking agent is an acrylo-siloxane.
5. A hydrogel according to claim 1 wherein the cross-linking agent is an acryloxy- or methacryloxyalkylpolyalkoxysilane.
6. A hydrogel according to claim 1 wherein the cross-linking agent is 3-methacryloxypropyltrimethoxysilane.

7. A hydrogel according to claim 1 wherein the source of calcium ions is calcium chloride, calcium bromide, or calcium phosphate.

8. A hydrogel according to claim 1 wherein the source of calcium ions and cross-linking agent are present in a molar ratio of between about 1:1 to about 3:1.

9. A hydrogel according to claim 1 wherein the source of calcium ions and cross-linking agent are present in a molar ratio of about 2:1.

10. A hydrogel according to claim 1 further comprising at least one calcium-binding component.

11. A hydrogel according to claim 10 wherein the calcium-binding component is poly(acrylic acid), acrylic acid, poly(methacrylic acid), methacrylic acid, or mixtures thereof, an amount of up to about 10% by weight.

12. A hydrogel according to claim 1 further comprising methyl methacrylate, poly(methyl methacrylate), vinyl acetate, poly(vinyl acetate), or mixtures thereof.

13. A hydrogel according to claim 12 wherein the methyl methacrylate, poly(methyl methacrylate), vinyl acetate, poly(vinyl acetate), or mixtures thereof are present in an amount of up to about 25% by weight.

14. A hydrogel according to claim 1 further comprising a medicament, an osteoclastic inhibitor, a pain reliever, or a chemotherapeutic agent, or mixtures thereof.

15. A hydrogel according to claim 1 further comprising radiopacifiers, radiomarkers, or radiopaque material.

16. A hydrogel according to claim 1 further comprising about 65-85 weight percent of water.

17. A hydrogel according to claim 1 further comprising about 75 weight percent of water.

18. A hydrogel according to claim 1 having an equilibrium viscosity of about 75-125 Poise.

19. A hydrogel according to claim 1 having an equilibrium viscosity of about 115-125 Poise.

20. A hydrogel according to claim 1 having an equilibrium viscosity of about 118 Poise.

21. A hydrogel according to claim 1 having an equilibrium viscosity of about 75-90 Poise.

22. A hydrogel according to claim 1 having an equilibrium viscosity of about 83 Poise.

23. A hydrogel according to claim 1 having an elastic modulus of about 0.5-0.9 MPa.

24. A hydrogel according to claim 1 having an elastic modulus of about 0.7 MPa.

25. A hydrogel according to claim 1, said hydrogel being prepared using N-alkylacrylamide.

26. A hydrogel according to claim 25 wherein the N-alkylacrylamide and poly(alkyleneglycol)di-acrylate or poly(alkyleneglycol)di-methacrylate are present in a ratio of from about 250:1 to about 150:1 by weight.

27. A hydrogel according to claim 25 wherein the N-alkylacrylamide and poly(alkyleneglycol)di-acrylate or poly(alkyleneglycol)di-methacrylate are present in a ratio of about 200:1 by weight.

28. A hydrogel according to claim 25 wherein the cross-linking agent and N-alkylacrylamide are present in a molar ratio of up to about 0.01.

29. A hydrogel according to claim 25 wherein the molar ratio of cross-linking agent:N-alkylacrylamide is between about 0.0005 and 0.01.

30. A hydrogel according to claim 25 wherein the molar ratio of cross-linking agent:N-alkylacrylamide is about 0.0005.

31. A hydrogel according to claim 25 wherein the molar ratio of cross-linking agent:N-alkylacrylamide is about 0.0075.

32. A hydrogel according to claim 25 wherein the molar ratio of cross-linking agent:N-alkylacrylamide is about 0.005.

33. A hydrogel according to claim 25 wherein the molar ratio of cross-linking agent:N-alkylacrylamide is about 0.003.

34. A hydrogel according to claim 25 wherein the molar ratio of cross-linking agent:N-alkylacrylamide is about 0.001.

35. A hydrogel according to claim 25 wherein the molar ratio of cross-linking agent:N-alkylacrylamide is about 0.01 fracture a hydrogel according to claim 1.

36. A method of reinforcing a vertebral bone structure comprising injecting into the vicinity of the bone structure a hydrogel according to claim 1.

37. A method of resurfacing an articulating joint comprising providing to the joint a hydrogel according to claim 1.

38. A method of preparing a hydrogel comprising:
  (a) providing a mixture of N-alkylacrylamide and poly(alkyleneglycol)di-acrylate or poly(alkyleneglycol)di-methacrylate in a solvent to form a first mixture;
  (b) adding a cross-linking agent, a source of calcium ions, and an initiator to the first mixture to form a second mixture;
  (c) polymerizing the second mixture for a time and at a temperature sufficient to cause polymerization to form a polymer;
  (d) drying the polymer;
  (e) pulverizing the polymer to form a powder; and
  (f) adding water to the powder.

39. The method of claim 38 wherein the N-alkylacrylamide and poly(alkyleneglycol)di-acrylate or poly(alkyleneglycol)di-methacrylate are present in a ratio of from about 250:1 to about 150:1 by weight.

40. The method of claim 38 wherein the N-alkylacrylamide and poly(alkyleneglycol)di-acrylate or poly(alkyleneglycol)di-methacrylate are present in a ratio of about 200:1 by weight.

41. The method of claim 38 wherein the N-alkylacrylamide is N-isopropylacrylamide.

42. The method of claim 38 wherein the poly(alkyleneglycol)di-acrylate or poly(alkyleneglycol)di-methacrylate is poly(ethyleneglycol)dimethacrylate or poly(propyleneglycol)dimethacrylate.

43. The method of claim 38 wherein the source of calcium ions is calcium chloride, calcium bromide, or calcium phosphate present in a molar ratio of about 2:1.

44. The method of claim 38 wherein the cross-linking agent is an acrylo-siloxane.

45. The method of claim 38 wherein the cross-linking agent is an acryloxy- or methacryloxyalkylpolyalkoxysilane.

46. The method of claim 38 wherein the cross-lining agent is 3-methacryloxypropyltrimethoxysilane.

47. A method of repairing a vertebral fracture comprising injecting into the vicinity of the fracture a hydrogel comprising:
  poly(N-alkylacrylamide),
  poly(alkyleneglycol)di-acrylate or poly(alkyleneglycol)di-methacrylate,
  cross-linking agent,
  a source of calcium ions, and
  water.

48. The method of claim 47 wherein the poly(N-alkylacrylamide) is poly(N-isopropylacrylamide).

49. The method of claim 47 wherein the poly(alkyleneglycol)di-acrylate or poly(alkyleneglycol)di-methacrylate is poly(ethyleneglycol)dimethacrylate.

50. The method of claim 47 wherein the poly(alkyleneglycol)di-acrylate or poly(alkyleneglycol)di-methacrylate is poly(propyleneglycol)dimethacrylate.

51. The method of claim 47 wherein the source of calcium ions is calcium chloride, calcium bromide, or calcium phosphate.

52. The method of claim 47 wherein the source of calcium ions and cross-linking agent are present in a molar ratio of about 2:1.

53. The method of claim 47 wherein the cross-linking agent is an acrylo-siloxane.

54. The method of claim 47 wherein the cross-linking agent is an acryloxy- or methacryloxyalkylpolyalkoxysilane, methacryloxypropyltrimethoxysilane.

55. The method of claim 47, said hydrogel being prepared using N-alkylacrylamide.

56. The method of claim 55 wherein the N-alkylacrylamide is N-isopropylacrylamide.

57. The method of claim 55 wherein the N-alkylacrylamide and poly(alkyleneglycol)di-acrylate or poly(alkyleneglycol)di-methacrylate are present in a ratio of from about 250:1 to about 150:1 by weight.

58. The method of claim 55 wherein the N-alkylacrylamide and poly(alkyleneglycol)di-acrylate or poly(alkyleneglycol)di-methacrylate are present in a ratio of about 200:1 by weight.

59. The method of claim 55 wherein the cross-linking agent and N-alkylacrylamide are present in a molar ratio of up to about 0.01.

60. A method of reinforcing a vertebral bone structure comprising injecting into the vicinity of the bone structure a hydrogel comprising:
poly(N-alkylacrylamide),
poly(alkyleneglycol)di-acrylate or poly(alkyleneglycol)di-methacrylate,
cross-linking agent,
a source of calcium ions, and
water.

61. The method of claim 60 wherein the poly(N-alkylacrylamide) is poly(N-isopropylacrylamide).

62. The method of claim 60 wherein the poly(alkyleneglycol)di-acrylate or poly(alkyleneglycol)di-methacrylate is poly(ethyleneglycol)dimethacrylate.

63. The method of claim 60 wherein the poly(alkyleneglycol)di-acrylate or poly(alkyleneglycol)di-methacrylate is poly(propyleneglycol)dimethacrylate.

64. The method of claim 60 wherein the source of calcium ions is calcium chloride, calcium bromide, or calcium phosphate.

65. The method of claim 60 wherein the source of calcium ions and cross-linking agent are present in a molar ratio of about 2:1.

66. The method of claim 60 wherein the cross-linking agent is an acryloxy- or methacryloxyalkylpolyalkoxysilane.

67. The method of claim 60 wherein the cross-linking agent is 3-methacryloxypropyltrimethoxysilane.

68. The method of claim 60, said hydrogel being prepared using N-alkylacrylamide.

69. The method of claim 68 wherein the N-alkylacrylamide is N-isopropylacrylamide.

70. The method of claim 68 wherein the N-alkylacrylamide and poly(alkyleneglycol)di-acrylate or poly(alkyleneglycol)di-methacrylate are present in a ratio of from about 250:1 to about 150:1 by weight.

71. The method of claim 68 wherein the N-alkylacrylamide and poly(alkyleneglycol)di-acrylate or poly(alkyleneglycol)di-methacrylate are present in a ratio of about 200:1 by weight.

72. The method of claim 68 wherein the cross-linking agent and N-alkylacrylamide are present in a molar ratio of up to about 0.01.

73. A method of resurfacing an articulating joint comprising providing to the joint a hydrogel comprising:
poly(N-alkylacrylamide),
poly(alkyleneglycol)di-acrylate or poly(alkyleneglycol)di-methacrylate,
cross-linking agent,
a source of calcium ions, and
water.

74. The method of claim 73 wherein the poly(N-alkylacrylamide) is poly(N-isopropylacrylamide).

75. The method of claim 73 wherein the poly(alkyleneglycol)di-acrylate or poly(alkyleneglycol)di-methacrylate is poly(ethyleneglycol)dimethacrylate.

76. The method of claim 73 wherein the poly(alkyleneglycol)di-acrylate or poly(alkyleneglycol)di-methacrylate is poly(propyleneglycol)dimethacrylate.

77. The method of claim 73 wherein the source of calcium ions and cross-linking agent are present in a molar ratio of about 2:1.

78. The method of claim 73 wherein the cross-linking agent is an acrylo-siloxane.

79. The method of claim 73 wherein the cross-linking agent is an acryloxy- or methacryloxyalkylpolyalkoxysilane.

80. The method of claim 73 wherein the cross-linking agent is 3-methacryloxypropyltrimethoxysilane.

81. The method of claim 73, said hydrogel being prepared using N-alkylacrylamide.

82. The method of claim 81 wherein the N-alkylacrylamide is N-isopropylacrylamide.

83. The method of claim 81 wherein the N-alkylacrylamide and poly(alkyleneglycol)di-acrylate or poly(alkyleneglycol)di-methacrylate are present in a ratio of from about 250:1 to about 150:1 by weight.

84. The method of claim 81 wherein the N-alkylacrylamide and poly(alkyleneglycol)di-acrylate or poly(alkyleneglycol)di-methacrylate are present in a ratio of about 200:1 by weight.

85. The method of claim 81 wherein the cross-linking agent and N-alkylacrylamide are present in a molar ratio of up to about 0.01.

* * * * *